United States Patent [19]

Batcho et al.

[11] 3,976,639

[45] Aug. 24, 1976

[54] INTERMEDIATES FOR INDOLES

[75] Inventors: Andrew David Batcho, Belleville; Willy Leimgruber, Montclair, both of N.J.

[73] Assignee: Hoffmann-La Roche Inc., Nutley, N.J.

[22] Filed: Mar. 31, 1975

[21] Appl. No.: 563,557

Related U.S. Application Data

[60] Continuation of Ser. No. 260,021, May 31, 1972, abandoned, which is a division of Ser. No. 86,953, Nov. 4, 1970, Pat. No. 3,732,245, which is a continuation-in-part of Ser. No. 879,619, Nov. 24, 1969, abandoned.

[52] U.S. Cl. .................... 260/240 D; 260/240 R; 260/319.1; 260/570.8 R
[51] Int. Cl.² ..................................... C07D 211/26
[58] Field of Search ............... 260/570.8 R, 240 R, 260/240 D

[56] References Cited
UNITED STATES PATENTS

| | | | |
|---|---|---|---|
| 3,530,120 | 9/1970 | Von Hirsch | 260/240 R |
| 3,732,245 | 5/1973 | Batcho et al. | 260/230 D X |

OTHER PUBLICATIONS

Robert Wahl, Doctoral Dissertation, Univ. of Stuttgart, frontispage and pp. 26–39, available to public Sept. 15, 1967 copies of correspondence from Stuggart, Radtke–Directress of Library and Prof. John E. Hiller showing proof of date Wahl Doctor Thesis available to public.

Meerwein et al., Annalen Der Chemie, vol. 641, pp. 1–39 (1961).

Chardonnens et al., Helv. Chim. Acta vol. 22, pp. 1471–1482 (1939).

Brederick et al. I, Chem. Ber. vol. 97, pp. 3397–3406 (1964).

Brederick et al. II, Chem. Ber. vol. 101, pp. 4048–4056 (1968).

*Primary Examiner*—John D. Randolph
*Attorney, Agent, or Firm*—Samuel L. Welt; Bernard S. Leon; William G. Isgro

[57] ABSTRACT

Ortho-nitrotoluenes are condensed with formamide acetals to yield the corresponding otho-nitro-β-aminestyrenes which undergo cyclization upon reduction to yield indoles.

14 Claims, No Drawings

INTERMEDIATES FOR INDOLES

CROSS-REFERENCE TO RELATED APPLICATIONS

This is a continuation, of application Ser. No. 260,021 filed May 31, 1972, now abandoned, which is a division of U.S. Pat. application Ser. No. 86,953 filed Nov. 4, 1970, now U.S. Pat. Nos. 3,732,245 issued May 8, 1973, which in turn is a continuation-in-part of U.S. Pat. application Ser. No. 879,619 filed Nov. 24, 1969, now abandoned.

BRIEF SUMMARY OF THE INVENTION

The invention relates to a process for preparing indoles which comprises condensing an ortho-nitrotoluene with a formamide acetal and subsequently reducing the resulting ortho-nitro-$\beta$-aminostyrene to yield the corresponding indole.

In another aspect, the invention relates to the intermediate ortho-nitro-$\beta$-aminostyrenes.

DETAILED DESCRIPTION OF THE INVENTION

The invention comprises a process and intermediates for preparing indole and substituted indoles.

More particularly, the invention comprises condensing a formamide acetal with an ortho-nitrotoluene to yield as an intermediate the corresponding ortho-nitro-$\beta$-aminostyrene and reducing said intermediate to yield the corresponding indole.

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl, and the like. The term "lower alkoxy" denotes an alkyl ether group in which the lower alkyl group is as described above, for example, methoxy, ethoxy, propoxy, pentoxy, and the like. The term "halogen" denotes the four halogens, i.e., bromine, chlorine, fluorine, and iodine. The term "aryl" denotes phenyl or phenyl bearing one or more substituents selected from the group consisting of halogen, trifluoromethyl, lower alkyl, lower alkoxy, nitro, amino, lower alkylamino, and di-lower alkylamino. The term "aryloxy" denotes an aryl ether group in which the aryl group is as described above, for example, phenoxy and the like. The term "acyl" denotes an alkanoyl group derived from an aliphatic carboxylic acid of 1 to 7 carbon atoms, for example, formyl, acetyl, propionyl, and the like; and an aroyl group derived from an aromatic carboxylic acid, such as benzoyl and the like. The term acyloxy denotes an alkanoyloxy group derived from an aliphatic carboxylic acid of 1 to 7 carbon atoms, for example, formyloxy, acetoxy, propionyloxy, and the like; and an aroyloxy group derived from an aromatic carboxylic acid, such as benzoyloxy and the like. The term lower alkylenedioxy denotes an alkylene diether group having from 1 to 7 carbon atoms such as methylenedioxy, ethylenedioxy, propylenedioxy, and the like. The term lower alkylene denotes a hydrocarbon radical of 2 to 5 carbon atoms, such as ethylene, propylene, butylene, and pentylene; preferred are those of 2 to 3 carbon atoms. The term ar-alkyl denotes a lower alkyl group in which one or more of the hydrogen atoms have been replaced by an aryl group. Exemplary is benzyl. The term cyclo-alkyl denotes a cyclic hydrocarbon of 3–6 carbon atoms, for example, cyclopentyl and the like.

Exemplary of aryl-lower alkoxy groups are benzyloxy, 1-phenylethyloxy, 2-chlorobenzyloxy, and the like. Exemplary of aryl-hydroxymethyl groups are phenylhydroxymethyl, p-chlorophenylhydroxymethyl, and the like. Exemplary of lower alkoxycarbonyl groups are methoxycarbonyl, ethoxycarbonyl, and the like. Exemplary of mono-lower alkylamino groups are methylamino, ethylamino, propylamino, isopropylamino, butylamino, pentylamino, and the like. Exemplary of di-lower alkylamino groups are dimethylamino, diethylamine, ethylmethylamino, dipropylamino, and the like. Exemplary of lower alkoxycarbonylamino groups are methoxycarbonylamino, ethoxycarbonylamino, and the like. Exemplary of aryl-lower alkoxycarbonylamino groups are benzyloxycarbonylamino, p-chlorobenzyloxycarbonylamino, and the like. Exemplary of acylamino groups are formamino, acetamino, propionylamino, benzoylamino, and the like. Exemplary of N-lower alkylacylamino groups are N-methylacetamino, N-methylformamino, N-ethylacetamino, and the like. Exemplary of di-lower alkylformamidino groups are dimethylformamidino, diethylformamidino, and the like.

In a preferred embodiment, the process of the invention is characterized by reaction scheme I:

REACTION SCHEME I

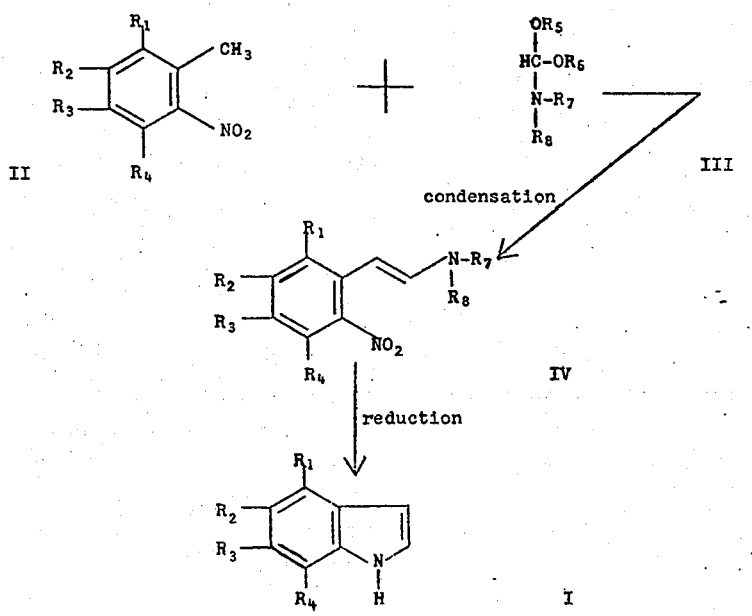

wherein $R_1$, $R_2$, $R_3$ and $R_4$, independently, are selected from the group consisting of hydrogen, lower alkyl, aryl, hydroxy, lower alkoxy, aryl-lower alkoxy, aryloxy, acyloxy, formyl, aroyl, hydroxymethyl, aryl-hydroxymethyl, carboxy, lower alkoxycarbonyl, carbamoyl, halogen, cyano, amino, mono-lower alkylamino, di-lower alkylamino, lower alkoxycarbonylamino, aryl-lower alkoxycarbonylamino, acylamino, N-lower alkylacylamino, di-lower alkylformamidino, di-lower alkoxymethyl, or nitro; $R_1$ and $R_2$, or $R_2$ and $R_3$, or $R_3$ and $R_4$, when taken together, are lower alkylenedioxy; $R_5$ and $R_6$, independently, are lower alkyl, and when taken together, are lower alkylene; and $R_7$ and $R_8$, independently, are lower alkyl and when taken together, are lower alkylene.

In a more preferred embodiment, the process of the invention is characterized by reaction scheme II:

REACTION SCHEME II

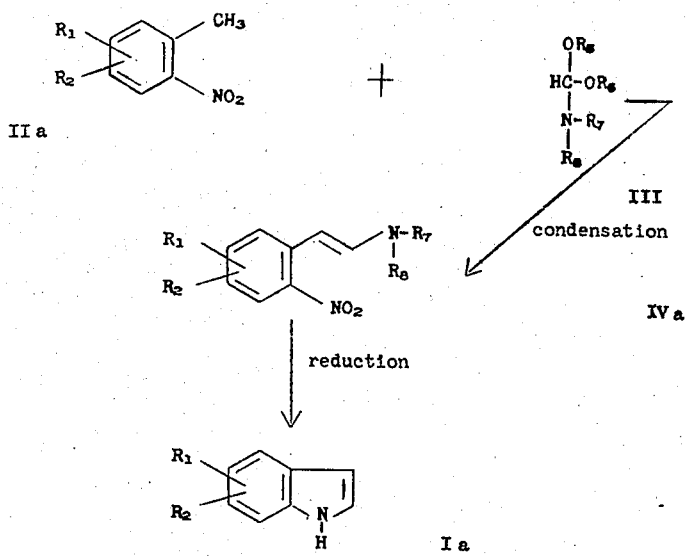

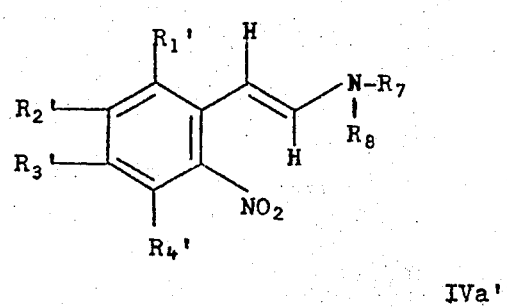

wherein $R_1$, $R_2$, $R_5$, $R_6$, $R_7$ and $R_8$ are as previously described. Preferably, $R_1$ and $R_2$, independently, are hydrogen, lower alkyl, hydroxy, lower alkoxy, aryl-lower alkoxy, acyloxy, formyl, aroyl, halogen, cyano, nitro, amino, or acylamino, and when taken together are lower alkylenedioxy; and $R_5$, $R_6$, $R_7$ and $R_8$, independently, are lower alkyl, and $R_5$ and $R_6$ or $R_7$ and $R_8$, when taken together, are lower alkylene.

In a most preferred embodiment of the invention, o-nitrotoluene is condensed with N,N-dimethylformamide dimethyl acetal to yield trans-β-dimethylamino-2-nitrostyrene. The latter is hydrogenated to yield indole.

In a further aspect, the invention relates to intermediates characterized by the formula

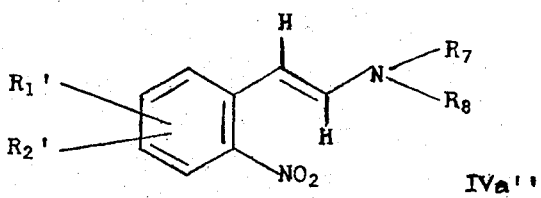

wherein $R_1'$, $R_2'$, $R_3'$ and $R_4'$, independently, are hydrogen, lower alkyl, lower alkoxy, aryl, formyl, aroyl, hydroxy, aryl-lower alkoxy, aryloxy, acyloxy, hydroxymethyl, aryl-hydroxymethyl, carboxy, lower alkoxycarbonyl, carbamoyl, halogen, cyano, amino, mono-lower alkylamino, di-lower alkylamino, lower alkoxycarbonylamino, aryl-lower alkoxycarbonylamino, acylamino, N-lower alkylacylamino, di-lower alkylformamidino, or di-lower alkoxymethyl; $R_1'$ and $R_2'$, $R_2'$ and $R_3'$, $R_3'$ and $R_4'$, when taken together, are lower alkylenedioxy; and $R_7$ and $R_8$ are as previously described.

In a further aspect, the invention relates to the intermediates characterized by the formula wherein $R_1'$ and $R_2'$, independently, are hydrogen, lower alkyl, lower alkoxy, aryl, formyl, aroyl, hydroxy, aryl-lower alkoxy, aryloxy, acyloxy, hydroxymethyl, aryl-hydroxymethyl, carboxy, lower alkoxy-carbonyl, carbamoyl, halogen, cyano, amino, mono-lower alkylamino, di-lower alkylamino, lower alkoxycarbonylamino, aryl-lower alkoxycarbonylamino, acylamino, N-lower alkylacylamino, di-lower alkylformamidino, or di-lower alkoxymethyl; $R_1'$ and $R_2'$, when taken together, are lower alkylenedioxy; and $R_7$ and $R_8$ are as previously described.

Preferably, in formula IVa'', $R_1'$ and $R_2'$, independently, are hydrogen, hydroxy, lower alkyl, lower alkoxy, formyl, aroyl, cyano, acyloxy, aryl-lower alkoxy, halogen, amino, or acylamino, and when taken together, are lower alkylenedioxy; and $R_7$ and $R_8$, independently, are lower alkyl.

It will be appreciated that the ortho-nitro-β-aminostyrenes of formulas IV, IVa, IVa' and IVa'' have the trans-configuration.

As is evident from the above, the present invention relates to a novel preparative route to indoles. It provides to the art a new and significant reaction route to many compounds of commercial value. The process is particularly salient in providing such compounds with greater efficiency than heretofore known in the prior art.

Broadly stated, the novel preparative path herein disclosed involves condensing the methyl function of an ortho-nitrotoluene with the formyl group of a formamide acetal, whereby a nitrobenzene derivative is obtained which bears a N,N-di-substituted aminovinyl function ortho to the nitro group, and thereafter by reducing the nitro group to an amino group which concurrently displaces the N,N-di-substituted amino function effecting cyclization to a compound having an indole nucleus.

The ortho-nitrotoluenes are known compounds or can be prepared by known procedures. Such compounds have monocyclic or bicyclic structures which may contain hetero atoms. Further, they may be unsubstituted or substituted independently with up to 4 moieties such as lower alkyl, aryl, hydroxy, lower alkoxy, aryl-lower alkoxy, aryloxy, acyloxy, formyl, aroyl, hydroxymethyl, arylhydroxymethyl, carboxy, lower alkoxycarbonyl, carbamoyl, halogen, cyano, nitro, amino, mono-lower alkylamino, di-lower alkylamino, lower alkoxycarbonylamino, aryl-lower alkoxycarbonylamino, acylamino, N-lower alkylacylamino, di-lower alkylformamidino or di-lower alkoxymethyl; or with up to 2 moieties of lower alkylenedioxy. Examples of such compounds are 3-methyl-4-nitrobiphenyl, 2-methyl-3-nitrobenzyl alcohol, 3-nitro-p-toluamide, 4-methyl-3-nitrobenzophenone, 3-nitro-p-toluic acid methyl ester, N,N-dimethyl-3-nitro-p-toluidine, 3-nitro-p-toluic acid, 4-methyl-3-nitrobenzophenone, N-methyl-3-nitro-p-toluidine, 3-nitro-p-toluidine, and the like.

The formamide acetals are known compounds or can be prepared by known procedures. Preferred formamide acetals are, for example, N,N-dimethylformamide diethyl acetal, N-N-dimethylformamide dimethyl acetal, N-formylpyrrolidine dimethyl acetal, 2-dimethylamino-1,3-dioxolane, N-formylpiperidine dimethyl acetal, N,N-dimethylformamide dibenzyl acetal, N,N-dimethylformamide dicyclohexyl acetal, N,N-dimethylformamide dineopentyl acetal, N,N-dimethylformamide di-isopropyl acetal, N,N-dimethylformamide di-n-heptyl acetal, and the like.

The condensation of the ortho-nitrotoluene, e.g., of formula II or IIa, with the formamide acetal, e.g., of formula III, can be effected in the presence or absence of an inert organic solvent. Preferably, the condensation is conducted in the presence of a polar aprotic solvent, such as, for example, N,N-dimethylformamide (DMF), diethyleneglycol dimethyl ether (Diglyme), hexamethylphosphortriamide (HMPT), and the like. The reaction conditions for the condensation are not narrowly critical. Thus, the condensation can be conducted at a temperature in the range of between about room temperature and the reflux temperature of the reaction mixture. Preferably, the reaction is conducted at a temperature in the range of 100°–160°. Most conveniently, the reaction is conducted at the reflux temperature of the reaction mixture. The condensation may be effected at atmospheric or super-atmospheric pressures. Conveniently, it is effected at atmospheric pressure.

The compounds of formulas IV$a'$ and IV$a''$ are novel compounds. In accordance with the invention, the ortho-nitro-$\beta$-aminostyrene intermediates, e.g., of formula IV or IV$a$, hereinafter referred to as aminostyrenes, are reduced chemically or catalytically to yield the corresponding indoles, e.g., of formula I or I$a$. The catalytic reduction may be effected in any conventional manner; preferably, it is effected at about room temperature with a hydrogen pressure of from about 1 to about 10 atmospheres. Any suitable hydrogenation catalyst may be employed, for example, a metal selected from the group consisting of chromium, molybdenum, tungsten, platinum, palladium, rhodium, cobalt, nickel, and ruthenium, their oxides, and combinations thereof, for instance, the oxides of cobalt or molybdenum in admixture and including cobalt molybdate. The preferred hydrogenating component is palladium, as well as other platinum group metals, or Raney nickel. Conveniently, the catalyst may be supported on charcoal, carbon or the like.

Advantageously, the catalyst may be utilized in the presence of an inert solvent, for example, an alkanol such as methanol, ethanol, and the like, a hydrocarbon such as benzene, toluene and the like; ethyl acetate; and DMF. Most preferably, benzene is utilized.

The chemical reduction may be effected in a conventional manner, for example, with a metal such as iron, zinc, tin, and the like, in an organic or inorganic acid such as acetic acid, hydrochloric acid, and the like; stannous chloride in hydrochloric acid, ferrous sulfate; sodium dithionite; sodium or ammonium sulfide or hydrosulfide; and the like. The reaction conditions for the chemical reduction are not critical. Preferably, it is effected at a temperature in the range of between about room temperature and reflux temperature of the reaction mixture, in the presence of a solvent such as water, or water miscible solvents, for example, alkanols such as methanol, ethanol or the like, or tetrahydrofuran.

While the substituents represented by $R_1$, $R_2$, $R_3$, and $R_4$ generally do not undergo a change during the condensation and subsequent reduction, in certain cases changes may occur. For instance, during the condensation, a carboxyl group may be converted to an ester group and a phenolic hydroxyl group may be converted to a phenolic ether. A dialkoxymethyl group can be retained or hydrolyzed depending on the work up. Thus, in the presence of acid, the dialkoxymethyl group is cleaved, and if no acid is present, it is retained.

Upon completion of the reaction, if desired, the end products, for example, indole, may be recovered utilizing conventional means such as crystallization, distillation or steam distillation and the like. The class of products resulting from the process of the invention, i.e., indole and the substituted indoles exemplified by formula I are well documented in the literature and are useful for many purposes, for example, as intermediates in the preparation of amino acids, alkaloids, tryptamines, and the like. Thus, for example, indole, 6-methoxyindole, and 5-benzyloxyindole can be utilized as intermediates in the preparation of tryptophan, reserpine, and serotonin, respectively, etc.

The following examples further illustrate the invention. All temperatures are in Centigrade degrees unless otherwise indicated.

EXAMPLE 1

Preparation of trans-$\beta$-dimethylamino-2-nitrostyrene

A one-liter three-necked flask fitted with a thermometer, a 15-cm. Vigreux column connected to a descending condenser and a receiver with a nitrogen inlet was charged with 137 g. of o-nitrotoluene, 191 g. of N,N-dimethylformamide diethyl acetal, and 235 ml. of N,N-dimethylformamide. The flask was immersed in a preheated oil bath which was maintained at 165° for 24 hours. The pot temperature was maintained at 145°–150° by continuous distillation of the formed ethanol.

The volatile components were removed by vacuum distillation under an atmosphere of nitrogen. The remaining dark red liquid was then transferred to a flask and distilled to yield 186 g. (97%) of trans-β-dimethylamino-2-nitrostyrene as a dark red liquid having a boiling point of 125°/ 0.03 mm.

Anal. Calcd. for $C_{10}H_{12}N_2O_2$: C, 62.48; H, 6.29; N, 14.58 Found: C, 62.66; H, 6.63; N, 14.50.

EXAMPLE 2

Preparation of trans-β-dimethylamino-2-nitrostyrene

In a one-liter three-necked flask fitted with a thermometer, a vacuum-jacketed, silvered column with Goodloe packing, distillation head and a receiver with a nitrogen inlet were placed 137.1 g. of o-nitrotoluene, 121.6 g. of 98% N,N-dimethylformamide dimethyl acetal, and 200.0 g. of N,N-dimethylformamide (DMF). The reaction mixture was heated at reflux for 24 hours. The reaction temperature was maintained at 135°–155° by continuous distillation of the methanol as formed. A total of 56.0 g. of distillate was collected.

By careful distillation 206.3 g. of DMF, b.p. 51°–55°/20 mm., and 13.0 g. (10%) of o-nitrotoluene, b.p. 109°/23 mm., were removed from the reaction mixture to give a residual dark liquid which after distillation yielded 167.0 g. (87%) of trans-β-dimethylamino-2-nitrostyrene as a dark red liquid having a boiling point of 128°/0.05 mm.

EXAMPLE 3

Preparation of trans-β-dimethylamino-2-nitrostyrene

A solution of 27.4 g. of o-nitrotoluene and 31.2 g. of 95% N,N-dimethylformamide diethyl acetal was heated under a nitrogen atmosphere in a 165° oil bath for 22 hours with continuous distillation of the ethanol formed in the reaction through a distillation head and descending condenser.

The volatile components were removed by vacuum distillation and then 20.2 g. (52%) of trans-β-dimethylamino-2-nitrostyrene was collected at boiling point 127°–29°/0.08 mm.

EXAMPLE 4

Preparation of trans-β-dimethylamino-2-nitrostyrene

A 50-ml. glass liner containing 15.6 g. of 95% dimethylformamide diethyl acetal and 13.7 g. of o-nitrotoluene was pressurized with nitrogen in an autoclave to 35 atm. and then heated to 155° for 24 hours.

The resulting red solution was distilled from a 50-ml. Claisen flask. The forerun (b.p. up to 60°/0.2 mm.) was discarded. The red liquid distilling at 134°–136°/0.25 mm. amounted to 13.4 g. (70%) of trans-β-dimethylamino-2-nitrostyrene.

EXAMPLE 5

Preparation of indole from trans-β-dimethylamino-2-nitrostyrene

A solution containing 178.6 g. of trans-β-dimethylamino-2-nitrostyrene in 2.5 liters of benzene containing 2.0 g. of 10% palladium on carbon was shaken in a 4-liter autoclave under an initial hydrogen pressure of 4.5 atm. until the absorption of hydrogen ceased. The catalyst was removed by filtration and was washed several times with benzene. The benzene solution was then extracted with 3 × 600 ml. of 1N sulfuric acid and 2 × 500 ml. of water. The aqueous phases were backwashed in a counter-current manner with 500 ml. of benzene. The combined benzene phases were dried over a mixture of anhydrous sodium sulfate and potassium carbonate, filtered, and evaporated to give 96.0 g. of greyish solid, which on rapid distillation under nitrogen gave 91.3 g. of a slightly yellowish solid having a melting point of 51°–53°. The distillate, on fractionation, gave a total of 87.4 g. (80%) of indole as a white solid having a melting point of 52.5°–53.5°.

EXAMPLE 6

Preparation of indole by reduction of trans-β-dimethylamino-2-nitrostyrene with iron and acetic acid.

In a 500-ml. three-necked flask fitted with a thermometer and mechanical stirrer were placed 19.2 g. of trans-β-dimethylamino-2-nitrostyrene, 100 ml. of 2B ethanol, and 100 ml. of glacial acetic acid followed by 41.9 g. of iron powder over a 5-min. period. The suspension was stirred for 2 hours during which time the temperature rose to 45° (the temperature was controlled by a water bath); then 30 ml. of 1n hydrochloric acid was added. The red color discharged and the temperature rose to about 45°. The reaction was allowed to stand for 18 hours and then was poured onto 1 l. of ice-water. To the resulting slurry was added 250 ml. of benzene; then both phases were filtered through a diatomaceous silica bed. The benzene layer was separated and the aqueous layer extracted once more with 200 ml. of benzene. The combined benzene extracts were washed successively with 2 × 200 ml. of 0.5N $H_2SO_4$ and 100 ml. of 10% $K_2CO_3$. The aqueous phases were backwashed in a counter-current manner with 100 ml. of benzene. The combined organic phases were dried ($Na_2SO_4$), filtered, and evaporated to give 4.2 g. of a brown solid which was dissolved in a minimum amount of benzene and was chromatographed on 50 g. of alumina (Woelm, activity III). Eluted fractions containing indole (pet. ether-benzene, 9:1) were pooled according to thin layer chromatography. Evaporation of the solvents and sublimation of the residue (40°–50° oil bath/0.03 mm.) yielded 2.02 g. (17%) of indole as white plates having a melting point of 51.5°–52.5°.

EXAMPLE 7

Preparation of indole by reduction of trans-β-dimethylamino-2-nitrostyrene with sodium dithionite To a stirred solution of 19.2 g. of trans-β-dimethylamino-2-nitrostyrene in 500 ml. of water and 200 ml. of methanol was added portionwise over 5 min. a mixture of 55.0 g. of sodium dithionite and 28.0 g. potassium carbonate while maintaining the temperature at 60°–65° by a water bath. A suspension formed; so 300 ml. of methanol was added and stirring was continued for 0.75 hour. To this were added 20 ml. of 30% ammonium hydroxide and, after removal of the methanol with a rotary evaporator, an additional 60 ml. of 30% ammonium hydroxide. The solution was then extracted with 3 × 400 ml. of benzene. The organic phases were backwashed in a counter-current manner with 100 ml. of water. The combined organic phases were dried ($Na_2SO_4$), filtered, and evaporated to give 3.5 g. of a dark brown solid which was dissolved in a minimum amount of benzene and chromatographed on 60 g. of alumina (Woelm, activity III). Eluted fractions (pet. ether) containing indole were pooled according to thin layer chromatography. Evaporation of the solvents and sublimation of the residue (2.4 g.) yielded 2.14 g. (18%) of indole having a melting point of 50°–52°.

EXAMPLE 8

Preparatiion of trans-2-nitro-β-pyrrolidinostyrene

In a 100-ml. three-necked flask fitted with a thermometer and 8-cm. Vigreux distillation head connected to a descending condenser and receiver with a nitrogen inlet were placed 6.85 g. of o-nitrotoluene, 7.25 g. of N-formylpyrrolidine dimethyl acetal, and 25 ml. of N,N-dimethylformamide. The flask was immersed in 160° oil bath for 1 hour during which time 2.8 ml. of methanol distilled. Volatile components were removed by vacuum distillation from a Claisen flask. A portion of the residue was distilled with partial decomposition in a short path distillation flask (bath 150°/0.1 mm.). The distillate was then vaporized twice in a molecular still (bath 110°/0.04 mm.), discarding a small amount of fore-run each time. In this way, 560 mg. of trans-2-nitro-β-pyrrolidinostyrene was obtained as a red liquid.

Anal. Calcd. for $C_{12}H_{14}N_2O_2$: C, 66.03; H, 6.47; N, 12.84 Found: C, 65.89; H, 6.45; N, 12.79.

EXAMPLE 9

Preparation of indole via trans-2-nitro-β-pyrrolidinostyrene

To a 100-ml. three-necked flask fitted with a thermometer and 8-cm. Vigreux column connected to a descending condenser and receiver with a nitrogen inlet was added 13.7 g. of o-nitrotoluene, 16.0 g. of N-formylpyrrolidine dimethyl acetal, and 50 ml. of N,N-dimethylformamide. The solution was then heated to 130°–150° for 1.5 hours, maintaining the temperature by continuous distillation of the methanol which formed in the reaction.

Removal of the volatile components by vacuum distillation (bath 50°/1 mm.) gave trans-2-nitro-β-pyrrolidinostyrene as a red liquid.

The product was dissolved in 100 ml. of benzene and was shaken in a hydrogen atmosphere with 440 mg. of 10% palladium on charcoal at an initial pressure of 3.5 atm. until hydrogen absorption ceased (3 equivalents). The catalyst was removed by filtration through a bed of diatomaceous silica and was washed with 3 × 50 ml. of benzene. The filtrate was then extracted consecutively with 2 × 200 ml. of 1M sulfuric acid, 2 × 200 ml. of water, and 100 ml. of 1M sodium carbonate. The aqueous phases were backwashed in a counter-current manner with 2 × 200 ml. of benzene. The combined organic phases were dried ($Na_2SO_4$), filtered, and evaporated (rotary evaporator) to give 11.0 g. of greenish solid, which on distillation gave 9.61 g. (82%) of indole, boiling point 78°/0.3 mm., melting point 50°–51.5°.

EXAMPLE 10

Preparation of trans-2-nitro-β-piperidinostyrene

In a 100 ml. three-necked flask fitted with a thermometer and 8-cm. Vigreux distillation head connected to a descending condenser and receiver with a nitrogen inlet were placed 6.85 g. of o-nitrotoluene, 8.76 g. of N-formylpiperidine dimethyl acetal, and 25 ml. of N,N-dimethylformamide. The flask was immersed in a 150° oil bath for 7 hours during which time 4 ml. of methanol distilled. Vacuum distillation from a Claisen flask afforded, after removal of the volatile components, three fractions: 2.86 g. (b.p. 144°–145°/0.06 mm.), 0.73 g. (b.p. 145°–146°10.06 mm.), and 5.35 g. (b.p. 146°–147°/0.07 mm.). The last fraction was pure trans-2-nitro-β-piperidinostyrene.

Anal. Calcd. for $C_{13}H_{16}N_2O_2$: C, 67.22; H, 6.94; N, 12.06 Found: C, 67.03; H, 7.08; N, 12.06.

EXAMPLE 11

Preparation of indole via trans-2-nitro-β-piperidinostyrene

In a 100 ml. three-necked flask fitted with a thermometer and 8-cm. Vigreux distillation head connected to a descending condenser and receiver with a nitrogen inlet were placed 13.40 g. of o-nitrotoluene, 13.40 g. of N-formylpiperidine dimethyl acetal, and 25 ml. of N,N-dimethylformamide. The solution was then heated to 130°–150° for 3 hours allowing the methanol to distill as it formed. Removal of the volatile components by vacuum distillation (water bath at 60°/0.5 mm.) gave trans-2-nitro-β-piperidinostyrene as a red liquid.

The trans-2-nitro-β-piperidinostyrene was dissolved in 250 ml. of benzene, 0.460 g. of 5% palladium on charcoal was added, and the suspension was shaken under an initial hydrogen pressure of 3.5 atm. until the absorption of hydrogen ceased (3 equivalents). The catalyst was removed by filtration and was washed several times with benzene. The filtrate was extracted with 3 × 100 ml. of 1M sulfuric acid, 100 ml. of water, 2 × 100 ml. of 1N sodium hydroxide, and 100 ml. of water. The aqueous phases were back-washed in a counter-current manner with 100 ml. of benzene. The combined organic phases were dried ($Na_2SO_4$), filtered, and evaporated to give 9.06 g. of a brown solid. Distillation in a Claisen flask gave 7.66 g. (70%) of indole, boiling point 60°–65°/0.06 mm., melting point 44°–49°.

EXAMPLE 12

Preparation of trans-β-dimethylamino-2,4-dinitrostyrene

A 250 ml. three-necked flask fitted with a thermometer and condenser with nitrogen inlet was charged with 18.21 g. of 2,4-dinitrotoluene and 18.00 g. of N,N-dimethylformamide diethyl acetal. The reaction vessel was then immersed in a 165° oil bath for 2 hours. The precipitate was triturated with ether and filtered. The resulting solid was crystallized from chloroformhexane (200 ml.) to yield 19.54 g. (82%) of trans-β-dimethylamino-2,4-dinitrostyrene as dark violet crystals having a melting point of 172.5°–174°.

EXAMPLE 13

Preparation of 6-aminoindole

A solution containing 4.75 g. of trans-β-dimethylamino-2,4-dinitrostyrene in 250 ml. of ethanol-N,N-dimethylformamide (4:1) was shaken with a teaspoonful of Raney nickel in a Parr apparatus under an initial hydrogen atmosphere of 3.5 atm. until hydrogen absorption ceased. The catalyst was removed by filtration through a bed of Celite* and washed with ethanol. The filtrate and washings were dried on a rotary evaporator. The residue was filtered in benzene through a dry column of 25 g. of Florisil** and the fractions containing the product were combined. The material was sublimed at 60°/0.05 mm. to give 600 mg. (23%) of 6-aminoindole as a white solid having a melting point of 77.5°–78.5°.

Anal. Calcd. for $C_8H_8N_2$: C, 72.71; H, 6.10; N, 21.19 Found: C, 72.50; H, 6.24; N, 21.28.

* diatomaceous silica ** magnesia - silica gel

EXAMPLE 14

Preparation of 5-benzyloxy-2-nitrotoluene

To a solution containing 15.3 g. of 3-methyl-4-nitrophenol in 200 ml. absolute ethanol stirred under nitrogen, 5.40 g. of sodium methoxide were added over a period of 15 minutes. The solution was then stirred at reflux for 1.5 hours. Thereafter, 12.66 g. of benzyl chloride were added dropwise, and the reaction was maintained at reflux for 20 hours. The ethanol was evaporated from the reaction mixture. To the residue were added 200 ml. of ether and 100 ml. 1N sodium hydroxide. The ether solution was washed with an additional 100 ml. of 1N sodium hydroxide solution and then with 100 ml. of water. The aqueous phases were washed with ether (3 × 300 ml.) in a counter-current manner. The combined aqueous phases were acidified with phosphoric acid and extracted with methylene chloride (3 × 200 ml.). The combined methylene chloride layers were dried ($Na_2SO_4$) and evaporated to dryness to give 2.8 g. (18%) of recovered 3-methyl-4-nitro-phenol. The ether extracts were dried ($Na_2SO_4$) and evaporated to dryness. The aqueous phases were discarded and the organic phases dried ($Na_2SO_4$) and evaporated to dryness. The product was crystallized from methanol (75 m.), yielding 15.1 g. (62%) of 5-benzyloxy-2-nitrotoluene as white needles having a melting point of 70.5°–71.5°.

Anal. Calcd. for $C_{14}H_{13}NO_3$: C, 69.13; H, 5.39; N, 5.76 Found: C, 69.34; H, 5.44; N, 5.69.

EXAMPLE 15

Preparation of trans-5-benzyloxy-β-dimethylamino-2-nitrostyrene

A 100-ml. three-necked flask fitted with a thermometer and a 15-cm. Vigreux column connected to a descending condenser and a receiver with a nitrogen inlet was charged with 24.32 g. of 5-benzyloxy-2-nitrotoluene, 23.0 g. of N,N-dimethylformamide diethyl acetal, and 25 ml. of N,N-dimethylformamide. The reaction vessel was then immersed in a 160° oil bath for 40 hours. The pot temperature was maintained above 140° by continuous distillation of the ethanol as it was formed.

The volatile components were removed under reduced pressure on a rotary evaporator. The red solid residue, crystallized from 300 ml. of ether and 25 ml. of benzene, yielded 23.3 g. (78%) of trans-5-benzyloxy-β-dimethylamino-2-nitrostyrene as red needles having a melting point of 97.5°–99°.

Anal. Calcd. for $C_{17}H_{18}N_2O_3$: C, 68.44; H, 6.08; N, 9.39 Found: C, 68.73; H, 6.13; N, 9.46.

EXAMPLE 16

Preparation of 5-benzyloxyindole

A solution containing 15.0 g. of trans-5-benzyloxy-β-dimethylamino-2-nitrostyrene in 250 ml. of 80% ethanol-N,N-dimethylformamide and 1 teaspoonful of Raney nickel were shaken under a hydrogen atmosphere in a Parr apparatus until hydrogen absorption ceased. The catalyst was removed by filtration. The solvents were removed under vacuum. The residue was sublimed and the sublimate was crystallized from ether-petroleum ether to yield 5.1 g. (45%) of 5-benzyloxyindole as white needles having a melting point of 103°–105°.

EXAMPLE 17

Preparation of trans-3-(β-dimethylaminovinyl)-4-nitrobenzoic acid ethyl ester A 100-ml. three-necked flask fitted with a thermometer and a 15-cm. Vigreux column connected to a descending condenser and a receiver with a nitrogen inlet was charged with 18.1 g. of 3-methyl-4-nitrobenzoic acid, 37.6 g. of N,N-dimethylformamide diethyl acetal, and 25 ml. of N,N-dimethylformamide. The reaction vessel was then immersed in a 100° oil bath for 4.5 hours. The pot temperature was maintained above 135° by continuous distillation of the ethanol formed in the reaction.

The volatile components were removed by vacuum distillation. After trituration with petroleum ether, the residue crystallized to give 18.5 g. (70%) of trans-3-(β-dimethylaminovinyl)-4-nitrobenzoic acid ethyl ester as a red solid having a melting point of 55°–56.5°.

Anal. Calcd. for $C_{13}H_{16}N_2O_4$: C, 59.08; H, 6.10; N, 10.60 Found: C, 59.02; H, 6.00; N, 10.63.

EXAMPLE 18

Preparation of 5-indolecarboxylic acid ethyl ester

A solution containing 7.5 g. of trans-3-(β-dimethylaminovinyl)-4-nitrobenzoic acid ethyl ester in 250 ml. of absolute ethanol and 715 mg. of 10% palladium on carbon were shaken under 3.5 atm. of hydrogen in a Parr apparatus until hydrogen absorption ceased. The catalyst was removed by filtration, and the filtrate was dried. The residue was applied to a Florisil* column (100 g.). The fractions containing the product (eluted with benzene) were combined. Crystallization from ether-petroleum ether yielded 2.1 g. (39%) of 5-indolecarboxylic acid ethyl ester as white crystals having a melting point of 95°–96°.

Anal. Calcd. for $C_{11}H_{11}NO_2$: C, 69.82; H, 5.86; N, 7.40 Found: C, 70.14; H, 5.87; N, 7.45.

* magnesia - silica gel

EXAMPLE 19

Preparation of trans-6-chloro-β-dimethylamino-2-nitrostyrene

A 250 ml. three-necked flask fitted with a thermometer and a 15-cm. Vigreux column connected to a descending condenser and receiver with a nitrogen inlet was charged with 17.16 g. of 2-chloro-6-nitrotoluene, 24 g. of N,N-dimethylformamide diethyl acetal, and 100 ml. of N,N-dimethylformamide. The reaction vessel was immersed in an oil bath, preheated to 160°, for 6 hours. The pot temperature was maintained about 140° by continuous distillation of the ethanol formed in the reaction.

The volatile components were removed by vacuum distillation at 25°/3 mm. and the product was distilled to give 20.2 g. (89%) of trans-6-chloro-β-dimethylamino-2-nitrostyrene as a dark red liquid having a boiling point of 111°/0.03 mm.

Anal. Calcd. for $C_{10}H_{11}ClN_2O_2$: C, 52.99; H, 4.89; Cl, 15.67; N, 12.36 Found C, 53.18; H, 4.57; Cl, 15.75 N, 12.23.

*magnesia - silica gel

EXAMPLE 20

Preparation of 4-chloroindole

To a solution containing 10.40 g. of trans-6-chloro-$\beta$-dimethylamino-2-nitrostyrene in 250 ml. of benzene in a 500-ml. Parr bottle was addded a half teaspoon of Raney nickel. The suspension was shaken under an initial hydrogen pressure of 3.5 atm. Until the absorption of hydrogen ceased. The catalyst was removed by filtration and was washed several times with benzene. The benzene filtrate was then extracted with 3 × 75 ml. of 1M sulfuric acid and 2 × 100 ml. of water. The aqueous phases were back-washed with 125 ml. of benzene in a counter-current manner. The combined benzene phases were dried ($K_2CO_3$), filtered, and evaporated to give 5.4 g. of dark green oil which, on distillation, yielded 4.75 g. of a yellow liquid having a boiling point of 116°/2 mm. After redistillation there was obtained 4.41 g. (63%) of 4-chloroindole as a slightly yellow liquid having a boiling point of 90°/0.04 mm.

EXAMPLE 21

Preparation of trans-5-chloro-$\beta$-dimethylamino-2-nitrostyrene

A 250-ml. three-necked flask fitted with a thermometer and a 15-cm. Vigreux column connected to a descending condenser and receiver with a nitrogen inlet was charged with 34.3 g. of 5-chloro-2-nitrotoluene, 55.0 g. of 85% N,N-dimethylformamide diethyl acetal, and 200 ml. of N,N-dimethylformamide. The reaction vessel was immersed in an oil bath, preheated to 160°, for 7 hours. The pot temperature was maintained above 146° by continuous distillation of the formed ethanol.

The volatile components were removed by vacuum distillation (70° bath/0.5 mm.). The resulting dark red residue was crystallized from ether-petroleum ether (275 ml.) to give 33.2 g. of red crystals having a melting point of 81.5°–82.5°. From the mother liquor an additional 6.6 g. of crystals having a melting point of 78°–81° was obtained. Thus, the total yield of trans-5-chloro-$\beta$-dimethylamino-2-nitrostyrene was 39.8 g. (88%).

Anal. Calcd. for $C_{10}H_{11}ClN_2O_2$: C, 52.99; H, 4.89; Cl, 15.64; N, 12.36 Found: C, 52.65; H, 5.20; Cl, 15.69; N, 11.89.

EXAMPLE 22

Preparation of 5-chloroindole

To a solution of 11.6 g. of trans-5-chloro-$\beta$-dimethylamino-2-nitrostyrene in 250 ml. of benzene in a 500-ml. Parr bottle was added a half teaspoon of Raney nickel. The suspension was shaken under an initial hydrogen pressure of 3.5 atm. until the absorption of hydrogen had ceased. The catalyst was removed by filtration and was washed several times with benzene. The benzene filtrate was then extracted with 2 × 100 ml. of 1N sulfuric acid, 2 × 100 ml. of water, and 100 ml. of 10% sodium bicarbonate solution. The aqueous phases were back-washed with 100 ml. of benzene in a counter-current manner. The combined benzene phases were dried ($Na_2SO_4$), filtered and evaporated to give 6.8 g. of greenish solid. Distillation yielded 6.26 g. of almost white solid which was dissolved in ether and percolated through about a gram of alumina. After removal of the ether, the residue was crystallized from 30 ml. of petroleum ether to give 6.0 g. (78%) of 5-chloroindole as white plates having a melting point of 71°–72°.

EXAMPLE 23

Preparation of trans-4-chloro-$\beta$-dimethylamino-2-nitrostyrene

In a 100 ml. three-necked round-bottom flask fitted with a thermometer and a condenser with a nitrogen inlet were placed 17.15 g. of 4-chloro-2-nitrotoluene and 18.00 g. of N,N-dimethylformamide diethyl acetal. The flask was immersed in a 145° oil bath for 58 hours. After 24 hours an additional 3 g. of acetal was added.

The volatile components were removed by vacuum distillation under nitrogen until the head temperature began to rise to 158°/0.09 mm. Subsequent distillation gave 12.0 g. (57%) of trans-4-chloro-$\beta$-dimethylamino-2-nitrostyrene as a red liquid having a boiling point of 158°/0.09 mm., which crystallized on standing to a solid having a melting point of 44°–46°.

Anal. Calcd. for $C_{10}H_{11}ClN_2O_2$: C, 52.99; H, 4.89; Cl, 15.63; N, 12.36 Found: C, 52.96; H, 4.89; Cl, 15.63; N, 12.30.

EXAMPLE 24

Preparation of 6-chloroindole

A solution of 4.50 g. of trans-4-chloro-$\beta$-dimethylamino-2-nitrostyrene in 250 ml. of absolute ethanol and 1 teaspoonful of Raney nickel were shaken under a hydrogen atmosphere until hydrogen absorption ceased. The catalyst was removed by filtration, and the filtrate was evaporated. The residue was applied to a Florisil column (25 g.). The fractions containing the product (eluted with 5% benzene-hexane) were combined. Crystallization from benzenehexane yielded 1.59 g. (52%) of 6-chloroindole as white crystals having a melting point of 89°–89.5°.

EXAMPLE 25

Preparation of trans-4-cyano-$\beta$-dimethylamino-2-nitrostyrene

A 500-ml. three-necked flask fitted with a thermometer and a 15-cm. Vigreux column connected to a descending condenser and receiver with a nitrogen inlet was charged with 24.3 g. of 3-nitrop-tolunitrile, 33.9 g. of N,N-dimethylformamide diethyl acetal, and 150 ml. of N,N-dimethylformamide. The reaction vessel was immersed in an oil bath, preheated to 160°, for 2.5 hours. The pot temperature was maintained above 140° by continuous distillation of the formed ethanol.

The volatile components were removed by vacuum distillation at 25°/0.5 mm. The resulting dark red solid residue was crystallized from 600 ml. of methanol, to yield 27.9 g. of trans-4-cyano-$\beta$-dimethylamino-2-nitrostyrene as red crystals having a melting point of 134°–137.5°.

Anal. Calcd. for $C_{11}H_{11}N_3O_2$: C, 60.82; H, 5.10; N, 19.55 Found: C, 60.89; H, 5.10; N, 19.09.

EXAMPLE 26

Preparation of 6-cyanoindole

A solution containing 10.85 g. of trans-4-cyano-$\beta$-dimethylamino-2-nitrostyrene in 500 ml. of benzene was separated into two equal portions and to each was added 215 mg. of 10% palladium on carbon. The suspensions were shaken under an initial hydrogen pressure of 3.5 atm. until the absorption of hydrogen ceased. The reaction was exothermic and was externally cooled with a stream of air. The catalyst was removed by filtration and washed several times with benzene. The benzene filtrates were combined and then extracted with 2 × 100 ml. of 1M sulfuric acid, 2 × 150 ml. of water, and 150 ml. of 10% sodium bicarbonate solution. The aqueous phases were back-washed with 100 ml. of benzene in a counter-current manner. The combined benzene phases were dried ($Na_2SO_4$), filtered, and evaporated to give 5.79 g. of solid which was dissolved in 150 ml. of benzene and filtered through 20 g. of alumina. After removal of the solvent, the residue was sublimed (110°/0.05 mm.) to give 5.39 g. of white crystalline material which, after crystallization from 30 ml. of benzene-petroleum ether, yielded 4.57 g. (65%) of 6-cyanoindole having a melting point of 128°–129°.

EXAMPLE 27

Preparation of 5,6-dimethylindole

A 500-ml. three-necked flask fitted with a thermometer and 15-cm. Vigreux column connected to a descending condenser with a receiver and nitrogen inlet was charged with 33.0 g. of 5-nitropseudocumene, 48.3 g. of N,N-dimethylformamide diethyl acetal, and 200 ml. of N,N-dimethylformamide. The reaction vessel was immersed in an oil bath, preheated to 165°, for 31 hours. The pot temperature was maintained above 140° by continuous distillation of the formed ethanol.

The volatile components were removed by vacuum distillation at 25°/0.5 mm. The residue was triturated with methanol and the insoluble material crystallized from 600 ml. methanol to give 25.5 g. (58%) of trans-$\beta$-dimethylamino-2,5-dimethyl-4-nitrostyrene as dark red needles having a melting point of 130°–131°.

Anal. Calcd. for $C_{12}H_{16}N_2O_2$: C, 65.43; H, 7.32; N, 12.72 Found: C, 65.17; H, 7.29; N, 12.88.

The methanol triturate was evaporated and the residue digested with petroleum ether (20 × 100 ml.). The petroleum ether extracts yielded 14.5 g. of red solid which after dissolution in 50 ml. of ethanol was added to a solution of 140 g. of ferrous sulfate heptahydrate, 500 ml. of water, and 85 ml. of concentrated ammonia. The resulting mixture was heated at reflux for 15 minutes, and the precipitate which formed was removed by filtration. The filtrate was concentrated by evaporation and then extracted with carbon tetrachloride (3 × 200 ml.). The combined organic phases were dried ($Na_2SO_4$), filtered, and evaporated. The residue was percolated through a dry column of alumina with 5% benzene-hexane. The fractions were combined and the solvents removed to give 450 mg. of a white solid. The material was crystallized from 8 ml. of petroleum ether to give 277 mg. of 5,6-dimethylindole as white needles having a melting point of 64.5°–65.5°.

EXAMPLE 28

Preparation of trans-$\beta$-dimethylamino-5-fluoro-2-nitrostyrene

A 250-ml. three-necked flask fitted with a thermometer and a 15-cm. Vigreux column connected to a descending condenser and receiver with a nitrogen inlet was charged with 20.00 g. of 5-fluoro-2-nitrotoluene, 56.0 g. of 85% N,N-dimethylformamide diethyl acetal, and 100 ml. of N,N-dimethylformamide. The reaction vessel was immersed in an oil bath, preheated to 160°, for 3.5 hours. The pot temperature was maintained above 140° by continuous distillation of the formed ethanol.

The volatile components were removed by vacuum distillation at 25°/0.5 mm., and the residual dark red solid was crystallized from 70 ml. of ether-petroleum ether to give 20.55 g. of red needles having a melting point of 52°–55°. The mother liquor, after removal of the solvents and distillation at 138°–140°/0.1 mm. yielded an additional 4.24 g. of red solid having a melting point of 56°–58°. Total yield was 24.79 g. (92%). A portion of the material was recrystallized to give trans-$\beta$-dimethylamino-5-fluoro-2-nitrostyrene as red crystals having a melting point of 56°–58°.

Anal. Calcd. for $C_{10}H_{11}FN_2O_2$: C, 57.14; H, 5.28; F, 9.03; N, 13.32 Found: C, 57.05; H, 5.36; F, 8.72; N, 13.39.

EXAMPLE 29

Preparation of 5-fluoroindole

To a solution of 10.51 g. of trans-$\beta$-dimethylamino-5-fluoro-2-nitrostyrene in 250 ml. of benzene in a 500-ml. Parr bottle was added a half teaspoon of Raney nickel. The suspension was shaken under an initial hydrogen pressure of 3.5 atm. until the absorption of hydrogen ceased. The catalyst was removed by filtration and washed several times with benzene. The benzene filtrate was then extracted with 2 × 100 ml. of 1M sulfuric acid, 2 × 150 ml. of water, and 150 ml. of 10% sodium bicarbonate solution. The aqueous phases were back-washed with 100 ml. of benzene in a counter-current manner. The combined benzene phases were dried ($Na_2SO_4$), filtered, and evaporated to give 5.23 g. of brown solid. Distillation (b.p. 85°/0.5 mm.) yielded 5.01 g. of yellowish solid, which upon crystallization from pentane yielded 2.36 g. of 5-fluoroindole as white leaflets having a melting point of 46.5°–47°. The mother liquor was percolated through 10 g. of alumina and the product eluted with ether. Sublimation of this material gave an additional 1.07 g. of product having a melting point of 46°–47°. Thus, the total yield was 3.44 g. (51%).

EXAMPLE 30

Preparation of trans-4-($\beta$-dimethylaminovinyl)-3-nitrobenzaldehyde dimethyl acetal A 250-ml. three-necked flask fitted with a thermometer and a 15-cm. Vigreux column connected to a descending condenser and receiver with a nitrogen inlet was charged with 11.18 g. of 4-methyl-3-nitrobenzaldehyde dimethyl acetal, 11.8 g. of N,Ndimethylformamide diethyl acetal, and 50 ml. of N,N-dimethylformamide. The reaction vessel was immersed in an oil bath, preheated to 160°, for 8 hours. The pot temperature was maintained above 140° by continuous distillation of the formed ethanol.

The volatile components were removed by vacuum distillation at 25°/0.5 mm. The dark red solid residue was triturated with cold methanol. The remaining solid was crystallized from 30 ml. of ether-pentane to obtain 7.22 g. of trans-4-($\beta$-dimethylaminovinyl)-3-nitrobenzaldehyde dimethyl acetal having a melting point of 67°–68.5°. The residue, obtained after evaporation of the mother liquor, was crystallized from 5 ml. of ether-pentane to give an additional 0.57 g. of product having a melting point of 66.5°–68.0°. Thus, the total yield was 7.79 g. (55%).

Anal. Calcd. for $C_{13}H_{18}N_2O_4$: C, 58.63; H, 6.81; N, 10.52 Found: C, 58.69; H, 6.75; N, 10.40.

EXAMPLE 31

Preparation of 6-formylindole

To a solution containing a 5.31 g. of trans-4-($\beta$-dimethylaminovinyl)-3-nitrobenzaldehyde dimethyl acetal in 250 ml. of benzene in a 500-ml. Parr bottle was added a half teaspoon of Raney nickel. The suspension was shaken under an initial hydrogen pressure of 3.5 atm. until the absorption of hydrogen ceased. The catalyst was removed by filtration and was washed several times with benzene. The residue, obtained by the evaporation of the benzene filtrate, was chromatographed on 150 g. alumina. The fractions eluted with 20% benzene-hexane followed by ether were combined and rechromatographed on 300 g. of alumina. The fractions eluted with ether were combined (1.33 g.) and crystallized from ether-pentane to give 0.76 g. (26%) of 6formylindole having a melting point of 127°–128.5°.

EXAMPLE 32

Preparation of 6-formylindole dimethyl acetal

To a solution containing 6.65 g. of trans-4-($\beta$-dimethylaminovinyl)-3-nitrobenzaldehyde dimethyl acetal in 125 ml. of benzene were added 1.0 g. potassium carbonate and 0.332 g. of 10% palladium on carbon. The suspension was stirred under an atmosphere of hydrogen. After the hydrogen absorption ceased, the catalyst was removed by filtration and was washed several times with benzene. Evaporation of the filtrate gave 4.95 g. of residue which on short-path distillation yielded 1.74 g. of purplish oil, which crystallized on cooling. Crystallization of this solid from 10 ml. of ether-petroleum ether yielded 1.18 g. of white solid having a melting point of 62°–63.5°. The mother liquor was applied to 10 g. of alumina and an additional 0.52 g. of the same product was eluted with 1:1 ether-petroleum ether. Recrystallization from ether-petroleum ether yielded 1.34 g. (27%) of 6-formylindole dimethyl acetal having a melting point of 62°–63.5°.

Anal. Calcd. for $C_{11}H_{13}NO_2$: C, 69.09; H, 6.35; N, 7.33 Found: C, 69.22; H, 6.76; N, 7.34.

EXAMPLE 33

Preparation of trans-4-($\beta$-dimethylaminovinyl)-3-nitrobenzaldehyde

A 100-ml. three-necked flask fitted with a reflux condenser with a nitrogen inlet was charged with 8.25 g. of 4-methyl-3-nitrobenzaldehyde, 11.1 g. of N,N-dimethylformamide diethyl acetal, and 50 ml. of N,N-dimethylformamide. The reaction vessel was immersed in an oil bath, preheated to 145°, for 45 minutes.

The volatile components were removed by vacuum distillation at 25°/0.5 mm. The dark red residue was triturated three times with 10 ml. of petroleum ether. The solid residue gave, on crystallization from methanol, 5.47 g. and on recrystallization from 100 ml. of methylene chloride-ether, 4.61 g. of trans-4-($\beta$dimethylaminovinyl)-3-nitrobenzaldehyde as red crystals having a melting point of 134°–136°. The residue obtained from the mother liquors was crystallized from 12 ml. of ethyl acetate to give an additional 2.21 g. of product having a melting point of 134°–136°. Thus, the total yield was 6.81 g. (62%).

Anal. Calcd. for $C_{11}H_{12}N_2O_3$: C, 59.99; H, 5.49; N, 12.72 Found: C, 60.23; H, 5.22; N, 12.66.

EXAMPLE 34

Preparation of trans-$\beta$-dimethylamino-4-isopropyl-2-nitrostyrene

In a 100-ml. three-necked flask fitted with a thermometer and 8-cm. Vigreux distillation head connected to a descending condenser and receiver with a nitrogen inlet were placed 17.9 g. of 2-nitro-p-cymene, 17.9 g. of N,N-dimethylformamide dimethyl acetal, and 25 ml. of N,N-dimethylformamide. The flask was immersed in a 150° oil bath for 42 hours, during which time 8 ml. of methanol distilled. The contents of the reaction vessel were transferred to a Claisen flask. Vacuum distillation, after removal of the more volatile components up to 130°/0.06 mm., afforded 19.61 g. (84%) of trans-$\beta$-dimethylamino-4-isopropyl-2-nitrostyrene as a red liquid (b.p. 138°–140°/0.06 mm.). An analytical sample obtained from a previous experiment gave:

Anal. Calcd. for $C_{13}H_{18}N_2O_2$: C, 66.64; H, 7.74; N, 11.95 Found: C, 66.69; H, 7.89; N, 11.95.

EXAMPLE 35

Preparation of 6-isopropylindole

A solution containing 11.71 g. of trans-$\beta$-dimethylamino-4-isopropyl-2-nitrostyrene in 125 ml. of benzene and 0.234 g. of 10% palladium on carbon were stirred under a hydrogen atmosphere. After hydrogen absorption ceased, the catalyst was removed by filtration and was washed several times with benzene. The benzene filtrate was then extracted with 2 × 50 ml. of 1N sulfuric acid, 100 ml. of water, and 50 ml. of 10% sodium bicarbonate solution. The aqueous phases were back-washed with 100 ml. of benzene in a counter-current manner. The combined benzene phases were dried ($Na_2SO_4$), filtered, and evaporated to give 7.47 g. of a green semi-solid. Trituration of this material with 3 × 20 ml. of ether gave 6.8 g. of ether-soluble green liquid which was distilled (b.p. 79°–87°/0.05 mm.). Crystallization of the yellow distillate from pentane yielded 4.04 g. (51%) of 6-isopropylindole having a melting point of 40°–41°.

Anal. Calcd. for $C_{11}H_{13}N$: C, 82.97; H, 8.23; N, 8.80 Found: C, 83.20; H, 8.23; N, 8.91.

EXAMPLE 36

Preparation of trans-$\beta$-dimethylamino-4-methoxy-2-nitrostyrene

In a 250-ml. three-necked flask fitted with a thermometer, a 15-cm. Vigreux column connected to a descending condenser and a receiver with a nitrogen inlet were placed 25.1 g. of 4-methyl-3-nitroanisole, 42.0 g. of 88% N,N-dimethylformamide diethyl acetal and 150 ml. of N,N-dimethylformamide. The flask was immersed in an oil bath, preheated to 165°, for 70 hours. The pot temperature was maintained above 140° by continuous distillation of the formed ethanol.

The volatile components were removed by vacuum distillation under nitrogen until the head temperature rose above 95°/0.05 mm. The remaining dark liquid was then transferred to a Claisen flask and distilled to yield 21.2 g. (64%) of trans-β-dimethylamino-4-methoxy-2-nitrostyrene as a dark red liquid having a boiling point of 152°/0.06 mm.

Anal. Calcd. for $C_{11}H_{14}N_4O_2$: C, 59.45; H, 6.35; N, 12.60 Found: C, 59.68; H, 6.53; N, 12.64.

EXAMPLE 37

Preparation of 6-methoxyindole

To a solution of 13.478 g. of trans-β-dimethylamino-4-methoxy-2-nitrostyrene in 250 ml. of benzene in a 500-ml. Parr bottle was added a half teaspoon of Raney nickel. The suspension was shaken under an initial hydrogen pressure of 3.5 atm. until hydrogen absorption ceased. The catalyst was removed by filtration and was washed several times with benzene. The benzene filtrate was then extracted with 2 × 100 ml. of 1M sulfuric acid, 2 × 100 ml. of water, and 100 ml. of 10% sodium bicarbonate solution. The aqueous phases were back-washed with 100 ml. of benzene in a counter-current manner. The combined benzene phases were dried ($Na_2SO_4$), filtered, and evaporated to give 6.7 g. of yellowish solid which, on distillation, yielded 5.64 g. (63%) of 6-methoxy-indole as an almost white solid having a melting point of 88°–90°.

EXAMPLE 38

Preparation of trans-β-dimethylamino-5-methoxy-2-nitrostyrene

A 250-ml. three-necked flask fitted with a thermometer and a 15-cm. Vigreux column connected to a descending condenser and receiver with a nitrogen inlet was charged with 16.7 g. of 5-methoxy-2-nitrotoluene, 32.3 g. of N,N-dimethylformamide diethyl acetal, and 100 ml. of N,N-dimethylformadide. The reaction vessel was then immersed in an oil bath, preheated to 165°, for 22 hours. The pot temperature was maintained above 140° by continuous distillation of the formed ethanol.

The volatile components were removed by vacuum distillation at 25°/0.5 mm. The resulting dark red solid residue was crystallized from 100 ml. of ether and 75 ml. of petroleum ether, and yielded 17.0 g. of trans-β-dimethylamino-5-methoxy-2-nitrostyrene as red crystals having a melting point of 67.5°–69.5°. The residue, obtained after evaporation of the mother liquor, was triturated with 10 ml. of ice-cold methanol. Recrystallization of the resulting solid (2.8 g.) from 10 ml. of methanol gave an additional 2.7 g. of product having a melting point of 68°–69°. Thus, the total yield was 19.7 g. (89%).

Anal Calcd. for $C_{11}H_{14}N_2O_3$: C, 59.45; H, 6.35; N, 12.60 Found: C, 59.53; H, 6.39; N, 12.65.

EXAMPLE 39

Preparation of trans-β-dimethylamino-5-methoxy-2-nitrostyrene

A solution of 8.35 g. of 3-methyl-4-nitroanisole, 14.58 g. of N,N-dimethylformamide dineopentyl acetal, and 50 ml. of N,N-dimethylformamide was heated at reflux under a nitrogen atmosphere for 41 hours and then was transferred to a Claisen flask. Vacuum distillation gave, after removal of the volatile components 4.75 g. of a red liquid (b.p. 152°/0.04 mm.) which crystallized on scratching to give a solid having a melting point of 61°–65°. Recrystallization from 70 ml. of ether-petroleum ether gave 3.70 g. (33%) of trans-β-dimethylamino-5-methoxy-2-nitrostyrene having a melting point of 68.5°–69.5°.

EXAMPLE 40

Preparation of trans-β-dimethylamino-5-methoxy-2-nitrostyrene

A solution of 3.0 g. of 3-methyl-4-nitroanisole, 5.1 g. of N,N-dimethylformaide dicyclohexyl acetal, and 25 ml. of N,N-dimethylformamide was heated at reflux under a nitrogen atmosphere for 40 hours and then was transferred to a Claisen flask. Vacuum distillation gave, after removal of the volatile components, 1.89 g. of a red liquid (b.p. 158°/0.04 mm.) which crystallized on scratching to give a solid, having a melting point of 61°–64°. Recrystallization from 10 ml. of ether and 7 ml. of petroleum ether gave 1.46 g (36%) of trans-β-dimethylamino-5-methoxy-2-nitrostyrene having a melting point of 67.5°–69°.

EXAMPLE 41

Preparation of trans-β-dimethylamino-5-methoxy-2-nitrostyrene

A solution of 16.71 g. of 3-methyl-4-nitroanisole, 30.00 g. of N,N-dimethylformamide dibenzyl acetal, and 50 ml. of N,N-dimethylformamide was heated at reflux under a nitrogen atmosphere for 17 hours and then was transferred to a Claisen flask. Vacuum distillation gave, after removal of the volatile components, 9.42 g. of a red liquid (b.p. 158°/0.10 mm.) which gave a tacky solid upon scratching. Recrystallization from 150 ml. of etherpetroleum ether gave 7.15 g. (32%) of trans-β-dimethylamino-5-methoxy-2-nitrostyrene having a melting point of 68.0°–69.5°.

EXAMPLE 42

Preparation of trans-β-dimethylamino-5-methoxy-2-nitrostyrene

A solution of 8.35 g. of 3-methyl-4-nitroanisole, 8.76 g. of N,N-dimethylformamide ethylene acetal (2-dimethylamino-1,3-dioxolane), and 25 ml. of N,N-dimethylformamide was heated at 150° under a nitrogen atmosphere for 53 hours and then was transferred to a Claisen flask. Vacuum distillation gave, after removal of the volatile components, 4.00 g. of a red liquid (b.p. 149°/0.07 mm.) which formed a gummy solid on scratching. Crystallization from 15 ml. of methanol gave 1.57 g. (14%) of trans-β-dimethylamino-5-methoxy-2-nitrostyrene having a melting point of 68°–69°.

EXAMPLE 43

Preparation of trans-5-methoxy-2-nitro-β-pyrrolidinostyrene

To a 100 -ml. three-necked flask fitted with a thermometer and 8-cm. Vigreux column connected to a descending condenser and receiver with a nitrogen inlet was added 8.35 g. of 3-methyl-4-nitroanisole, 8.0 g. of N-formylpyrrolidine dimethyl acetal, and 25 ml. of N,N-dimethylformamide. The solution was heated at 135° for two hours with continuous distillation of the methanol which formed in the reaction.

Removal of the volatile components under vacuum (40° bath/1 mm.) and recrystallization of the red residue from 75 ml. of methanol gave, in two crops, 11.7 g. (94%) of red needles, melting point 71°–72°.

Recrystallization of a portion of the first crop from methanol gave an analytical sample of trans-5-methoxy-2-nitro-β-pyrrolidinostyrene, melting point 71°–72°.

Anal. Calcd. for $C_{13}H_{16}N_2O_3$: C, 62.89; H, 6.50; N, 11.28 Found: C, 62.87; H, 6.58; N, 11.24.

EXAMPLE 44

Preparation of 5-methoxyindole

To a solution containing 11.11 g. of trans-β-dimethylamino-5-methoxy-2-nitrostyrene in 250 ml. of benzene in a 500-ml. Parr bottle was added 230 mg. of 10% palladium on carbon. The suspension was shaken under an initial hydrogen pressure of 3.5 atm. until the absorption of hydrogen had ceased. The catalyst was removed by filtration and was washed several times with benzene. The benzene filtrate was then extracted with 2 × 100 ml. of 1M sulfuric acid, 2 × 100 ml. of water, and 100 ml. of 10% sodium bicarbonate solution. The aqueous phases were back-washed with 100 ml. of benzene in a counter-current manner. The combined benzene phases were dried ($Na_2SO_4$), filtered and evaporated to give 5.45 g. of a brown solid. Distillation yielded 5.26 g. (72%) of 5-methoxyindole as a slightly yellowish liquid, having a boiling point of 108°/0.3 mm., which crystallized on cooling to an off-white solid having a melting point of 56°–57°.

EXAMPLE 45

Preparation of 4,5-methylenedioxy-2-nitrotoluene

A solution containing 75.0 g. of piperonal, 200 ml. of glacial acetic acid, and 1 ml. of conc. hydrochloric acid was shaken with 4 g. of 10% palladium on carbon in an autoclave under an initial hydrogen pressure of 35 atm. until hydrogen absorption ceased. The catalyst was removed by filtration.

The filtrate was transferred to a three-neck flask fitted with a thermometer, mechanical stirrer, and a dropping funnel. A solution containing 80.0 ml. of conc. nitric acid in 200 ml. of glacial acetic acid was added to the reaction vessel with stirring over a period of 1 hour. The reaction vessel was maintained below 10° by means of an ice-acetone bath. After the addition was complete, the reaction mixture was allowed to reach room temperature and was then poured over a mixture of sodium hydroxide and ice. The resulting suspension was extracted with (chloride 94 × 1000 ml.). The combined organic phases were dried ($Na_2SO_4$), filtered, and evaporated to give a yellow solid, which after crystallization from 300 ml. of ethanol, gave 76.5 g. (84%) 0f 4,5-methylenedioxy-2-nitrotoluene as yellow needles having a melting point of 85°–86.5°.

EXAMPLE 46

Preparation of trans-β-dimethylamino-4,5-methylenedioxy-2-nitrostyrene

A 250-ml. three-necked flask fitted with a thermometer and a 15-cm. Vigreux column connected to a descending condenser with a receiver and a nitrogen inlet was charged with 18.1 g. of 4,5-methylenedioxy-2-nitrotoluene, 20 g. of N,N-dimethylformamide diethyl acetal, and 100 ml. of N,N-dimethylformamide. The reaction vessel was immersed in a 165° oil bath for 17.5 hours. The pot temperature was maintained above 140° by continuous distillation of the formed ethanol.

The volatile components were removed by vacuum distillation at 25°/0.05 mm. The reside was crystallized from 300 ml. of ethanol to give 17.0 g. (72%) of trans-β-dimethylamino.4,5-methylenedioxy-2-nitrostyrene as red-brown crystals having a melting point of 114°–116°.

Anal. Calcd. for $C_{11}H_{12}N_2O_4$: C, 55.93; H, 5.12; N, 11.86 Found: C, 56.09; H, 5.17; N, 11.56.

EXAMPLE 47

Preparation of 5,6-methylenedioxyindole

A solution containing 11.83 g. of trans-β-dimethylamino-4,5-methylenedioxy-2-nitrostyrene in 250 ml. of benzene was shaken with 1 teaspoonful of Raney nickel under an initial hydrogen pressure of 3.5 atm. until hydrogen absorption ceased. The catalyst was removed by filtration and washed several times with benzene. The filtrate and washings were washed with 1M sulfuric acid (2 × 100 ml.), 100 ml. of water, and 100 ml. of 10% sodium bicarbonate. The combined organic phases were dried ($Na_2SO_4$), filtered and evaporated to give 5.52 g. of a brown solid. A solution of the residue in benzene was percolated through a column of alumina. The eluate, after evaporation of the solvent, was sublimed at 110°/0.2 mm. to give 5.2 g. of a white solid which, upon crystallization from methylene chloride-hexane, yielded 4.50 g (50%) of 5,6-methylenedioxyindole as white needles having a melting point of 109.5°–110.5°.

EXAMPLE 48

Preparation of trans-β-dimethylamino-6-methyl-2-nitrostyrene

A 250-ml. three-necked flask fitted with a thermometer and a 15-cm. Vigreux column connected to a descending condenser and receiver with a nitrogen inlet was charged with 15.22 g. of 3-nitro-o-xylene, 20.00 g. of N,N-dimethylformamide diethyl acetal, and 100 ml. of N,N-dimethylformamide. The reaction vessel was immersed in an oil bath, preheated to 160°, for 24 hours. The pot temperature was maintained above 140° by continuous distillation of the formed ethanol.

The volatile components were removed by vacuum distillation until the head temperature began to rise above 90°/0.1 mm. Further distillation yielded 14.54 g. (70%) of trans-β-dimethylamino-6-methyl-2-nitrostyrene as a dark red liquid having a boiling point of 108°10.05 mm.

Anal. Calcd. for $C_{11}H_{14}N_2O_2$: C, 64.06; H, 6.84; N, 13.58 Found: C, 63.79; H, 7.28; N, 13.71.

EXAMPLE 49

Preparation of 4-methylindole

To a solution containing 9.327 g. of trans-β-dimethylamino-6-methyl-2-nitrostyrene in 250 ml. of benzene in a 500-ml. Parr bottle was added a half teaspoon of Raney nickel. The suspension was shaken under an initial hydrogen pressure of 3.5 atm. until the absorption of hydrogen had ceased. The catalyst was removed by filtration and washed several times with benzene. The benzene filtrate was then extracted with 2 × 100 ml. of 1M sulfuric acid, 2 × 100 ml. of water, and 100 ml. of 10 % sodium bicarbonate soltuion. The aqueous phases were back-washed with 150 ml. of benzene in a counter-current manner. The combined benzene phases were dried ($Na_2SO_4$), filtered, and evaporated to give 3.89 g. of a brown oil which after two distillations yielded 3.37 g. (57%) of 4-methylindole as a yellow liquid having a boiling point of 82°/0.4 mm.

EXAMPLE 50

Preparation of trans-β-dimethylamino-3-methyl-2-nitrostyrene

A 500-ml. three-necked flask fitted with a thermometer, a 15-cm. Vigreux column connected to a descending condenser and receiver with a nitrogen inlet was charged with 30.23 g. of 2-nitro-m-xylene, 64.77 g. of N,N-domethylformamide diethyl acetal, and 200 ml. of N,N-dimethylformamide. The reaction vessel was then immersed in an oil bath, preheated to 165°, for 46 hours. The pot temperature was maintained above 140° by continuous distillation of the formed ethanol.

The volatile components were removed by vacuum distillation at 25°/0.5 mm. The resulting dark red liquid residue was distilled under vacuum, the forerun (15.32 g., b.p. 93°–99°/0.2 mm.) was a mixture of trans-β-dimethylamino-3-methyl-2-nitrostyrene and 2-nitro-m-xylene (ratio of 3:5 resp.). Subsequent fractions yielded 16.60 g. (40%) of trans-β-dimethylamino-3-methyl-2-nitrostyrene as a red liquid (b.p. 116°–117°/0.04 mm.) which crystallized on cooling and had a melting point of 75°–77°.

Anal. Calcd. for $C_{11}H_{14}N_2O_2$: C, 64.06; H, 6.84; N, 13.58 Found: C, 63.95; H, 6.70; N, 13.37.

EXAMPLE 51

Preparation of 7-methylindole

To a solution containing 10.31 g. of trans-β-dimethylamino-3-methyl-2-nitrostyrene in 250 ml. of benzene was added 103 mg. of 10% palladium on carbon. The suspension was shaken under an initial hydrogen pressure of 3.5 atm. until the absorption of hydrogen had ceased. The catalyst was removed by filtration and was washed several times with benzene. The benzene filtrate was then extracted with 2 × 100 ml. of 1M sulfuric acid, 100 ml. of water, and 100 ml. of 10% sodium bicarbonate solution. The aqueous phases were back-washed with 100 ml. of benzene in a counter-current manner. The combined benzene phases were dried ($Na_2SO_4$), filtered and evaporated to give 4.628 g. of residue which, on distillation under vacuum, gave 4.203 g. (b.p. 109°/0.9 mm.) of light tan solid. Filtration of the distillate through 50 g. of alumina and crystallization from 30 ml. of ether-petroleum ether gave 3.15 g. (48%) of 7-methylindole as white crystals having a melting point of 83°–84°.

EXAMPLE 52

Preparation of trans-β-dimethylamino-4,5-dimethoxy-2-nitrostyrene

A 1-l. three-necked flask fitted with a thermometer and a 15-cm. Vigreux column connected to a descending condenser with a receiver and nitrogen inlet was charged with 98.6 g. of 4,5-dimethoxy-2-nitrotoluene, 500 ml. of N,N-dimethylformamide, and 120 g. of N,N-dimethylformamide dimethyl acetal. The reaction temperature was maintained at 140° for 42 hours. The volatile compounds were removed by vacuum distillation at 25°/0.1 mm. to give a solid residue of crude trans-β-dimethylamino-4,5-dimethoxy-2-nitrostyrene.

From a previous experiment, an analytical sample of trans-β-dimethylamino-4,5-dimethoxy-2-nitrostyrene, a red solid, m.p. 125°–126°, was obtained by crystallization from methanol.

Anal. Calcd. for $C_{12}H_{16}N_2O_4$: C, 57.13; H, 6.39; N, 11.11 Found: C, 57.47; H, 6.65; N, 11.35.

EXAMPLE 53

Preparation of 5,6-dimethoxyindole

To a solution of the crude trans-β-dimethylamino-4,5-dimethoxy-2-nitrostyrene obtained in Example 52 in 2.0 l. of benzene was added 10 g. of 10% palladium on carbon and the suspension was shaken under an initial hydrogen pressure of 7 atm. After hydrogen absorption ceased (3 equivalents), the catalyst was filtered and washed with 2 l. of benzene. The combined filtrate and washings were concentrated to 2 l. in vacuo and the organic phase washed with 3 × 300 ml. of 1N sulfuric acid, 200 ml. of 1N sodium hydroxide and 200 ml. of water. The aqueous phases were back-washed in a counter-current manner with 500 ml. of benzene. The combined organic phases were dried ($Na_2SO_4$) and filtered through 280 g. of silica gel. The filtrate was evaporated and the residue triturated with ether. The residual white solid was crystallized from 700 ml. of benzene to give (in two crops) 24.5 g. (28%) of 5,6-dimethoxyindole as white crystals, m.p. 154°–155°.

EXAMPLE 54

Preparation of trans-4,5-dibenzyloxy-β-dimethylamino-2-nitrostyrene

In a 1-l. three-necked flask fitted with a thermometer and 8-cm. Vigreux distillation head connected to a descending condenser and receiver with a nitrogen inlet were placed 87.3 g. of 4,5-dibenzyloxy-2-nitrotoluene, 38.0 g. of N,N-dimethylformamide dimethyl acetal, and 250 ml. of N,N-dimethylformamide. The solution was heated at 140° for 48 hours with continuous removal of the methanol as it formed. The volatile components were removed by vacuum distillation (bath temperature 65°/0.1 mm.). Crystallization of the residue from methanol (2.5 l.) yielded (two crops) 86.8 g. (86%) of red solid, m.p. 99°–100°.

An analytical sample, obtained from a previous experiment, was characterized as trans-4,5-dibenzyloxy-β-dimethylamino-2-nitrostyrene, m.p. 99.5°–101°.

Anal. Calcd. for $C_{24}H_{24}N_2O_4$: C, 71.27; H, 5.98; H, 6.93 Found: C, 71.09; H, 6.30; N, 6.83.

EXAMPLE 55

Preparation of 5,6-dibenzyloxyindole

To a solution of 10.11 g. of trans-4,5-dibenzyloxy-β-dimethylamino-2-nitrostyrene in 250 ml. of benzene in a 500-ml. Parr bottle was added a teaspoon of Raney nickel. The suspension was shaken under an initial hydrogen pressure of 3.5 atm. until the absorption of hydrogen ceased. The catalyst was removed by filtration and washed several times with benzene. The benzene filtrate was extracted with 3 × 100 ml. of 1N sulfuric acid, 250 ml. of water, 3 × 100 ml. of 1N sodium hydroxide and 250 ml. of water. The aqueous phases were back-washed in a counter-current manner with 100 ml. of benzene.

The combined organic phases were dried ($Na_2SO_4$), filtered and evaporated to give 7.67 g. of a brown solid which was dissolved in a minimum amount of benzene and was chromatographed on 40 g. of silica gel prepared in hexane. Eluted fractions [benzene-hexane (1:1)] were pooled according to thin layer chromatography. Evaporation of the solvents and recrystallization of the residue (5.8 g.) from benzene-hexane yielded 4.34 g. (54% of 5,6-dibenzyloxyindole as white needles, m.p. 112°–113°.

We claim:

1. A compound of the formula

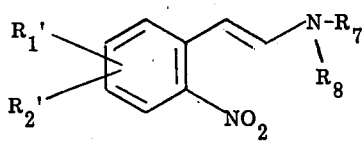

wherein $R_1'$ is hydrogen, lower alkoxy, formyl, phenyl-lower alkoxy, halogen or di-lower alkoxymethyl, $R_2'$ is lower alkoxy, formyl, phenyl-lower alkoxy, halogen or di-lower alkoxymethyl, and when taken together, $R_1'$ and $R_2'$ are methylenedioxy; $R_7$ and $R_8$, independently, are lower alkyl, and when taken together, are piperidino or pyrrolidino.

2. A compound in accordance with claim 1, wherein $R_1'$ is hydrogen and $R_2'$ is lower alkoxy.

3. A compound in accordance with claim 2, trans-β-dimethylamino-4-methoxy-2-nitrostyrene.

4. A compound in accordance with claim 1, wherein $R_1'$ is hydrogen and $R_2'$ is phenyl-lower alkoxy.

5. A compound in accordance with claim 4, trans-5-benzyloxy-β-dimethylamino-2-nitrostyrene.

6. A compound in accordance with claim 1, wherein $R_1'$ is hydrogen and $R_2'$ is halogen.

7. A compound in accordance with claim 6, trans-5-chloro-β-dimethylamino-2-nitrostyrene.

8. A compound in accordance with claim 1, trans-2-nitro-β-piperidinostyrene.

9. A compound in accordance with claim 1, trans-2-nitro-β-pyrrolidinostyrene.

10. A compound in accordance with claim 1, trans-β-dimethylamino-4,5-dimethoxy-2-nitrostyrene.

11. A compound in accordance with claim 1, trans-4,5-dibenzyloxy-β-dimethylamino-2-nitrostyrene.

12. A compound in accordance with claim 1, trans-β-dimethylamino-4,5-methylenedioxy-2-nitrostyrene.

13. A compound in accordance with claim 1, trans-4-(β-dimethylamino-vinyl)-3-nitrobenzaldehyde.

14. A compound in accordance with claim 1, trans-4-(β-dimethylamino-vinyl)-3-nitrobenzaldehyde dimethylacetal.

* * * * *